United States Patent [19]

Whitten

[11] Patent Number: 5,538,958
[45] Date of Patent: *Jul. 23, 1996

[54] NMDA ANTAGONISTS

[75] Inventor: Jeffrey P. Whitten, Cincinnati, Ohio

[73] Assignee: Merrell Pharmaceuticals Inc., Cincinnati, Ohio

[ * ] Notice: The term of this patent shall not extend beyond the expiration date of Pat. No. 5,326,756.

[21] Appl. No.: 468,098

[22] Filed: Jun. 6, 1995

Related U.S. Application Data

[62] Division of Ser. No. 359,678, Dec. 20, 1994, Pat. No. 5,500,419, which is a continuation of Ser. No. 229,250, Apr. 18, 1994, abandoned, which is a division of Ser. No. 917,723, Jul. 20, 1992, Pat. No. 5,326,756, which is a continuation of Ser. No. 790,291, Nov. 8, 1991, abandoned, which is a division of Ser. No. 553,431, Jul. 20, 1990, Pat. No. 5,095,009, which is a continuation-in-part of Ser. No. 508,333, Apr. 11, 1990, abandoned, which is a continuation-in-part of Ser. No. 409,478, Sep. 19, 1989, abandoned.

[51] Int. Cl.$^6$ .................................................. A61K 31/66
[52] U.S. Cl. .................................................. 514/114
[58] Field of Search .................................................. 514/114

[56] References Cited

U.S. PATENT DOCUMENTS

| | | | |
|---|---|---|---|
| 4,705,781 | 11/1987 | Boast | 514/85 |
| 4,746,653 | 5/1988 | Hutchison et al. | 514/89 |
| 4,761,405 | 8/1988 | Rzeszotarski et al. | 514/114 |
| 4,906,621 | 3/1990 | Hutchison et al. | 514/89 |
| 5,049,555 | 9/1991 | Rzeszotarski et al. | 514/114 |
| 5,095,009 | 3/1992 | Whitten et al. | 514/85 |
| 5,217,963 | 6/1993 | Hutchison et al. | 514/82 |
| 5,326,756 | 7/1994 | Whitten et al. | 514/114 |
| 5,395,827 | 3/1995 | Rzeszotarski et al. | 514/114 |

FOREIGN PATENT DOCUMENTS

| | | |
|---|---|---|
| 0159889 | 4/1985 | European Pat. Off. . |
| 233154 | 8/1987 | European Pat. Off. . |
| 2156818 | 10/1985 | United Kingdom . |

OTHER PUBLICATIONS

Dorland's Illustrated Medical Dictionary 26th Ed., Saunders, Philadelphia (1981) pp. 644–681.
Pike, et al, Chem Abstracts, vol. 98, No. 13635 (1983).
Wedler et al, Arch. Biochem. Biophys. 202, pp. 482–490 (1980).
Derwent Abstracts 88–251384/36 (Abstract of DE 3804–936–A).
Bennett et al., Life Sciences, vol. 39, pp. 2455–2461.
Pike et al, Biochimica et Biophysica Acta. 708 (1982) 203–209.
Whitten, et al.; J. Med Chem, vol. 33, pp. 2961–3 (1990).
Kehne, et al. Chem. Abstr. vol. 114, entry 199543e (1991).
Kehne et al. Eur. Journal Pharm. vol. 193; pp. 283–92 (1991).
Annual Reports in Medicinal Chemistry, vol. 22, *Excitatory Amino Acids and Mammalian CNS Function*, Lehmann, et al.; pp. 31–40. (1987).
Annual Reports in Medicinal Chemistry, vol. 24, *Recent Advances in Excitatory Amino Acid Research*, Graham Johnson, pp. 41–50. (1989).
Annual Reports in Medicinal Chemistry, vol. 26, *Recent Advances in Excitatory Amino Acid Research*, Johnson, et al.; pp. 11–22. (1991).

*Primary Examiner*—Donald G. Daus
*Attorney, Agent, or Firm*—J. Michael Dixon

[57] ABSTRACT

The present invention is directed to a new class of beta-ketone, beta oxime and beta hydrazine phosphonate NMDA antagonists.

1 Claim, No Drawings

NMDA ANTAGONISTS

This is a division of application Ser. No. 08/359,678, filed Dec. 20, 1994, now U.S. Pat. No. 5,500,419, which is a continuation of application Ser. No. 08/229,250, filed Apr. 18, 1994, now abandoned, which is a divisional of application Ser. No. 07/917,723, filed Jul. 20, 1992, issued as U.S. Pat. No. 5,326,756, on Jul. 5, 1994, which is a continuation of Ser. No. 07/790,291, filed Nov. 8, 1991, now abandoned, which is a divisional of Ser. No. 07/553,431, filed on Jul. 20, 1990 which issued as U.S. Pat. No. 5,095,009 on Mar. 10, 1992, which is a continuation-in-part of application Ser. No. 07/508,333, filed Apr. 11, 1990, now abandoned, which is a continuation-in-part of application Ser. No. 07/409,478, filed Sep. 19, 1989, now abandoned.

The present invention is directed to a new class of beta ketone, beta oxime and beta hydrazine phosphonate NMDA antagonists. Another aspect of the invention is directed to the treatment of epilepsy, nerve trauma such as that caused by stroke, cardiac arrest, hypoglycemia, and physical damage to either the brain or spinal cord, neurogenerative diseases, anxiety and for the relief of pain. A further aspect of the invention is directed to pharmaceutical compositions containing these NMDA antagonists.

A new class of excitatory amino acid antagonists which act at the NMDA receptor complex have been discovered which can be described by the following formulae:

$$\begin{matrix} & O & \\ & \| & \\ HO - & P - OR & \\ & | & \\ & CR_1R_2 & \\ & \diagdown & \\ & & C=O \\ & \diagup & \\ & A & \\ & | & \\ & B & \end{matrix}$$
FORMULA I $$\begin{matrix} & O & \\ & \| & \\ HO - & P - OR & \\ & | & \\ & CR_1R_2 & \\ & \diagdown & \\ & & C=M \\ & \diagup & \\ & A & \\ & | & \\ & B & \end{matrix}$$
FORMULA Ia in which R is represented by hydrogen, $C_{1-4}$ alkyl, or $-CF_3$; $R_1$ and $R_2$ are each independently represented by hydrogen, $C_{1-4}$ alkyl, cycloalkyl, alkylphenyl, $-CF_3$, phenyl or substituted phenyl; M is represented by $N-O-R_3$ or $N-NH-R_3$, in which $R_3$ is represented by hydrogen, $C_{1-4}$ alkyl or alkylphenyl; A is represented by a methylene or a trimethylene bridging group, either of which may be optionally substituted with up to 2 substituents selected from the group consisting of $-CF_3$, $C_{1-4}$ alkyl, cycloalkyl, alkylphenyl, phenyl, substituted phenyl; and B is represented by one of the following substituents:

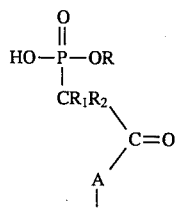, 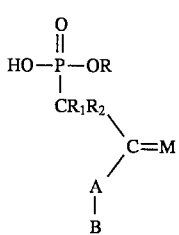, $H_2N-CH-COOZ$ or $H_2N-CX-COOZ$ in which Z is represented by hydrogen, $C_{1-4}$ alkyl, cycloalkyl, trialkylamino, alkylphenyl, phenyl, or substituted phenyl; and x is represented by alkyl, alkylphenyl, or trifluoromethyl; the pharmaceutically acceptable acid addition salts thereof; the pharmaceutically acceptable basic addition salts thereof, the tautomers thereof, the optical isomers thereof, and the geometric isomers thereof; with the following proviso's: a) in Formula I, when R, $R_1$, and $R_2$ are hydrogen, A is an unsubstituted methylene, and B is represented by $H_2N-CH-COOZ$, in which Z is hydrogen; then the compound is not present as its L-isomer; b) at least one of the substituents represented by R, $R_1$ and $R_2$ must be a hydrogen atom; c) when B is represented by either a piperazine derivative or an α-substituted amino acid then at least one of the substituents represented by $R_1$ and $R_2$ must be a hydrogen atom, and; d) when B is represented by an oxazolone derivative, then R must be hydrogen.

As used in this application:

a) the terms "lower alkyl group and $C_{1-4}$ alkyl" refer to a branched or straight chained alkyl group containing from 1–4 carbon atoms, such as methyl, ethyl, n-propyl, isopropyl, n-butyl, isobutyl, etc;

b) the terms "lower alkoxy group and $C_{1-4}$ alkoxy" refer to a straight or branched alkoxy group containing from 1–4 carbon atoms, such as methoxy, ethoxy, n-propoxy, isopropoxy, n-butoxy, isobutoxy, etc.;

c) the term "cycloalkyl" refers to a cyclohexyl or a cyclopentyl group;

d) the term "substituted phenyl ring" refers to a phenyl ($C_6H_5$) which is substituted with up to 3 substituents, each substituent is independently selected from the group consisting of halogens, $C_{1-4}$ alkyl, $C_{1-4}$ alkoxy, $CF_3$, $OCF_3$, OH, CN, $NO_2$, $COOR_3$, and $CONR_3R_4$ in which $R_3$ and $R_4$ are represented by hydrogen or a $C_{1-4}$ alkyl. These substituents may be the same or different and may be located at any of the ortho, meta, or para positions.

e) the term "alkylphenyl substituent" refers to the following structure $-(CH_2)_m-C_6H_5$, in which m is an integer from 1–3. This phenyl ring may be substituted in the manner described immediately above.

f) the term "piperazine derivative" refers to:

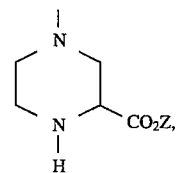

g) the term "α-substituted amino acid" refers to $H_2N-CX-COOZ$ h) the term "oxazolone" refers to:

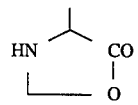

i) the term "trialkylamino" refers to:

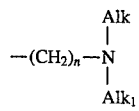

in which n is represented by an integer from 2–4 and Alk and Alk1 are each independently represented by a $C_{1-4}$ alkyl.

j) the term "oxime" refers to compounds in which M is represented by: N—O—R₃, k) the term "hydrazine" refers to compound in which M is represented by: N—NH—R₃, and m) the term "halogen" refers to a chlorine, fluorine or bromine atom.

The expression "pharmaceutically acceptable acid addition salts" is intended to apply to any non-toxic organic or inorganic acid addition salt of the base compounds represented by Formulae I, Ia or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formulae I, Ia, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Some of the compounds of Formulae I and Ia exist as optical isomers. Any reference in this application to one of the compounds represented by Formulae I or Ia is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

Examination of Formula I shows that the beta ketone phosphonates of Formula I will exist in a state of tautomeric equilibrium in which the carbonyl function will participate in a keto-enol equilibrium reaction. As is obvious to those skilled in the art, when the compound exists in its enol form then both $R_1$ and $R_2$ will not be bonded to the indicated carbon atom. Thus only those compounds in which either $R_1$ or $R_2$ is hydrogen will exhibit this tautomerism. This tautomerism may be depicted as follows:

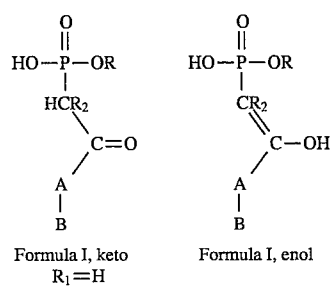

Formula I, keto $R_1=H$    Formula I, enol

The enol tautomer will exist as geometric isomers due to the presence of the double bond. This enol will exist as the following cis and trans isomers:

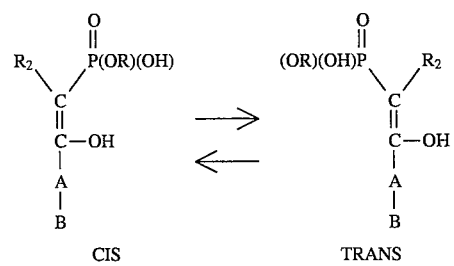

CIS    TRANS

In those compounds of Formula I in which A is represented by a trimethylene moiety, another equilibrium reaction will be established in which the compounds undergo an intramolecular condensation to form a cyclic imine. One example of such a ketone-imine equilibrium reaction is depicted below:

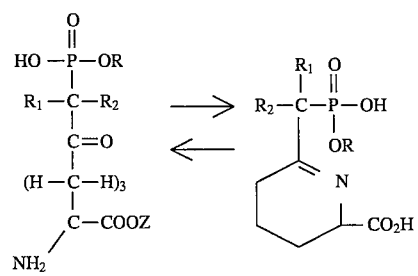

In the compounds of Formula Ia in which M is an oxime derivative, it is possible for the oxime substituent to exist in one of two configurations, either syn or anti.

Any reference to the compounds of Formula I or Ia should be construed as encompassing the keto forms of these compounds, the enol form of these compound in either the cis or trans configuration, the cyclic imine form of these compounds, the syn or anti oxime derivative, etc. It is also intended for the claims to encompass these compounds as well.

Illustrative examples of compounds encompassed by Formula I include:

a) R-4-Oxo-5-phosphononorvaline b) R-2-Amino-6-oxo-7-phosphonoheptanoic acid c) 4-(2-Oxo-3-phosphonopropyl)-2-piperazine carboxylic acid d) R-4-(2-Oxo-3-phosphonopropyl)-5-oxo-3-oxazolidine e) 4-Oxo-5-phosphono-2-methylnorvaline f) 4-Oxo-5-phosphono-3-methylnorvaline g) R-4-Oxo-5-phosphono-5-methylnorvaline h) 4-Oxo-5-phosphono-3,5-dimethylnorvaline i) 5-(Hydroxymethoxyphosphinyl)-4-oxonorvaline
j) 4-Oxo-5-phosphono-2-(2-phenylethyl)norvaline
k) 4-Oxo-5-phosphono-5-(2-phenylethyl)norvaline
l) R-4-Oxo-5-phosphononorvaline ethyl ester
m) R-2-Amino-6-oxo-7-phosphonoheptanoic acid ethyl ester
n) 4-Oxo-5-phosphono-2-methylnorvaline ethyl ester
o) R-4-Oxo-5-phosphono-5-methylnorvaline benzyl ester
p) 4-Oxo-5-phosphono-2-(4'-trifluoromethylphenylethyl)norvaline
q) 4-(2-Oxo-3-phosphonopropyl)-2-piperazine carboxylic acid ethyl ester
r) 4-(Hydroxyimino)-5-phosphononorvaline
s) 4-(Methoxyimino)-5-phosphononorvaline
t) 4-(Benzylhydrazino)-5-phosphononorvaline
u) 4-[(Phenylmethoxy)imino]-5-phosphononorvaline
v) R-4-Oxo-5-phosphononorvaline methyl ester
w) 4-[(2'-Phenylethoxy)imino]-5-phosphononorvaline.

As with any class of medicinal agents, certain of the compounds of Formulae I and Ia are preferred due to their superior potency, bioavailability characteristics, etc. It is preferred for A to be represented by a methylene moiety, and for B to be represented by either a piperazine derivative or an amino acid, which may be optionally substituted at the α-position.

Illustrative examples of preferred compounds include:

a) R-4-Oxo-5-phosphononorvaline
b) R-4-Oxo-5-phosphononorvaline ethyl ester
c) R-4-Oxo-5-phosphono-5-methylnorvaline
d) R-4-Oxo-5-phosphono-5-methylnorvaline ethyl ester
e) 4-(2-Oxo-3-phosphonopropyl)-2-piperazinecarboxylic acid
f) 4-(2-Oxo-3-phosphonopropyl)-2-piperazinecarboxylic acid ethyl ester
g) R-4-Oxo-5-phosphono-2-methylnorvaline
h) R-4-Oxo-5-phosphono-2-methylnorvaline ethyl ester
i) 4-(Hydroxyimino)-5-phosphononorvaline
j) 4-(Methoxyimino)-5-phosphononorvaline
k) 4-[(Phenylmethoxy)imino]-5-phosphononorvaline
l) R-4-Oxo-5-phosphononorvaline methyl ester,
m) 4-[(2'-Phenylethoxy)imino]-5-phosphononorvaline.

The compounds of Formula I can be prepared using techniques well known in the art.

Those compounds in which B is represented by an amino acid or a derivative of an amino acid (ie. $H_2N-CH-COOZ$) and R is represented by a hydrogen atom can be prepared using the methodology depicted below in Reaction Scheme I:

REACTION SCHEME I

STEP A

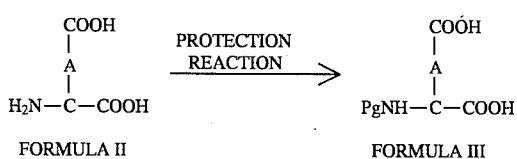

FORMULA II → FORMULA III

-continued
REACTION SCHEME I

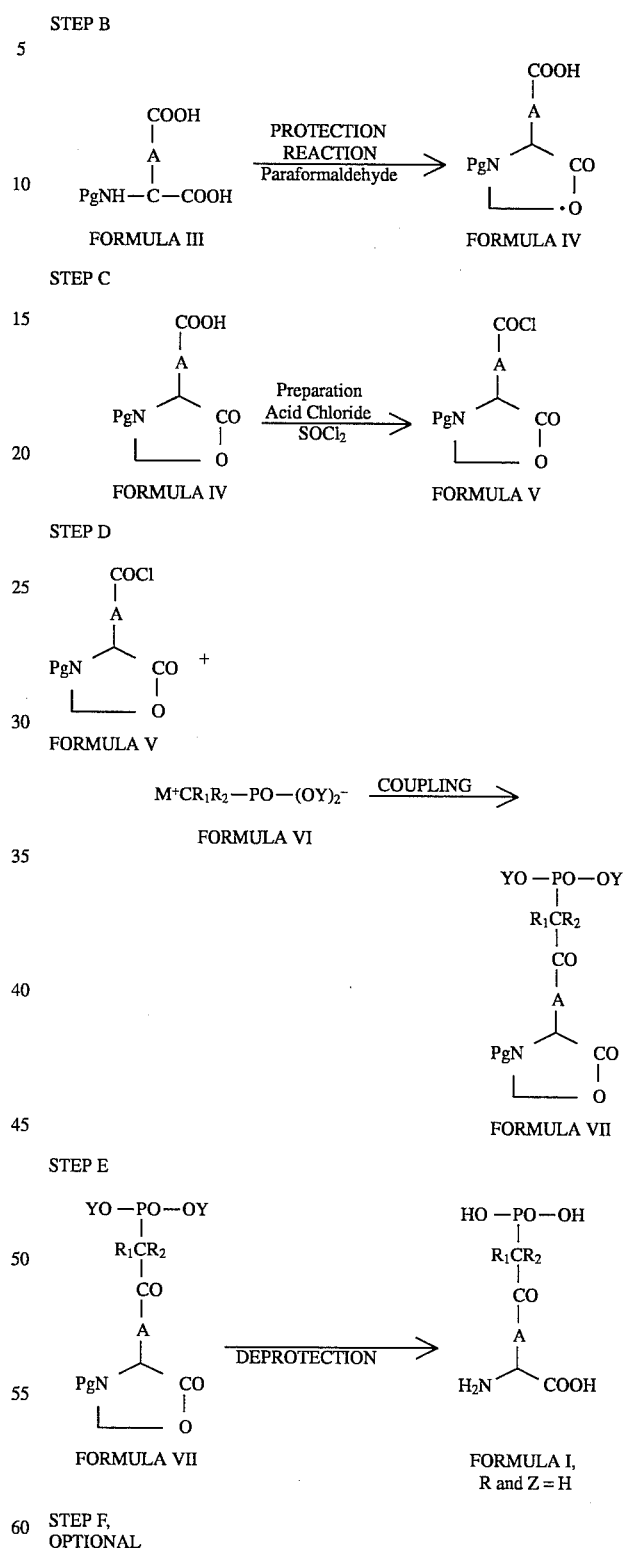

-continued
REACTION SCHEME I

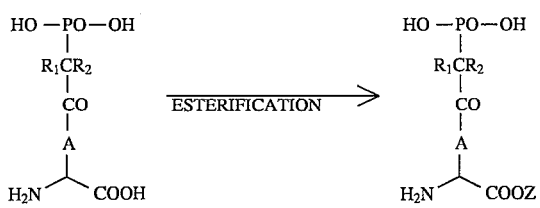

In Step A of Reaction Scheme I, an amino acid as described by Formula II in which A is as in Formula I is subjected to a protection reaction in which a benzyl carbamate protecting group (Pg) is placed on the free amine of the amino acid thereby producing the protected amino acid of Formula III. In Step B of Reaction Scheme I, the protected amino acid of Formula III is contacted with paraformaldehyde thereby further protecting the amino acid by converting it into an oxazolone derivative as described by Formula IV. In Step C, the oxazolone is contacted with thionyl chloride which introduces an acid chloride function into the molecule thereby producing the acid chloride of Formula V.

In Step D, the acid chloride of Formula V is subjected to a coupling reaction, optionally in the presence of a transition metal catalyst, with the phosphonate of Formula VI in which $R_1$ and $R_2$ are as in Formula I, M is represented by a suitable cation, and each Y is independently represented by a $C_{1-4}$ alkyl. This coupling reaction produces the protected beta ketone phosphonate derivative of Formula VII in which A, $R_1$, $R_2$, and Y are as above. In Step E, a deprotection reaction is conducted which serves to remove all of the protecting groups from the beta keto phosphonate molecule. This reaction removes the benzyl carbamate protecting group, the oxazolone protecting group, and the alkyl groups represented by Y. In optional Step F, an ester function can be introduced at the phosphonic acid function of the final product of Formula I.

The proper starting material in Step A of Reaction Scheme I is an amino acid in which A is represented by the same methylene or trimethylene function as that desired in the final product of Formula I. The protection reaction of Step A can be carried out using techniques well known in the art. Typically the amino acid of Formula II is contacted with from 1 to 1.5 equivalents of benzyl chloroformate at approximately room temperature in about a 0.05 to 0.2 molar solution of sodium hydroxide. The reactants are typically stirred together for a period of time ranging from about 1 to 3 days. The protected amino acid of Formula III can be recovered from the reaction using techniques known in the art such as extraction with an organic solvent or concentration.

The protection reaction of Step B, in which the oxazolone protecting group is placed on the protected amino acid of Formula III, can be carried out using methods known in the art. The amino acid of Formula III is typically contacted with from about 2 to 3 equivalents of paraformaldehyde in the presence of an acid catalyst such as para-toluene sulfonic acid. The catalyst is typically present in the reaction zone in a quantity of from about 1 to 3 w/w % relative to the quantity of amino acid utilized. The reactants are typically stirred together in an organic solvent such as benzene at a temperature range of from 40° C. to reflux for a period of time ranging from about 1 to 4 hours.

The oxazolone of Formula IV can be recovered from the reaction using techniques known in the art such as either concentration or extraction. If desired, the protected amino acid of Formula IV can be purified by selective acid, base, and organic solvent extractions.

The next step in the reaction is to prepare the acid chloride of Formula V as is depicted in Step C. This acid chloride can be prepared using techniques known in the art. Typically the oxazolone of Formula IV is contacted with from about 3 to 4 equivalents of thionyl chloride. The reaction can be carried out neat or in a solvent such as chloroform. The reaction is allowed to proceed for a period of time ranging from 10 to 20 minutes at reflux. After the reaction is completed, the acid chloride of Formula V can be recovered from the reaction by concentration under vacuum.

In Step D of the reaction, the acid chloride of Formula V is subjected to a coupling reaction with a phosphonate as described by Formula VI. The appropriate phosphonate is one in which $R_1$ and $R_2$ are represented by the same substituents as that in the desired product of Formula I. The alkyl functions represented by Y in the phosphonate are not retained in the final product. The cation represented by M is typically Li or Zn. The phosphonates of Formula VI are known in the art as are methods for their preparation.

This coupling reaction can be carried out using techniques well known in the art. Typically equimolar amounts of the phosphonate and a suitable base, such as n-butyl lithium, are contacted to form a cation of the phosphonate. This is then treated with approximately a 10% mole excess of the acid chloride in the presence of a transition metal catalyst such as copper iodide. The catalyst is typically present in the reaction zone in an equivalent amount. The reactants are typically contacted at a temperature range of from about −78° to room temperature for a period of time ranging from about 2 to 16 hours. The resulting protected beta ketone phosphonate derivative of Formula VII can be recovered from the reaction zone by either concentration or extraction as is known in the art. If desired, the beta ketone phosphonate can be purified by chromatographic techniques known in the art such as flash chromatography.

The deprotection reaction depicted in Step E can be carried out using techniques known in the art. This deprotection reaction serves to remove the benzyl carbamate protecting group (Pg), the oxazolone protecting group and the alkyl groups represented by Y, thereby producing some of the beta ketone phosphonates of Formula I. Typically, the protected beta ketone phosphonate derivative of Formula VII is contacted with a stoichometric amount of trimethylsilyl iodide (TMSI, about 4 equivalents) in a solvent such as methylene dichloride. The deprotection reaction is typically carried out at room temperature for a period of time ranging from about 3 to 5 hours. The quantity of trimethylsily iodide which is utilized is important. Failure to use stoichometric quantities of the TMSI will produce a compound in which not all of the protecting groups have been removed.

If Z is to be represented by a substituent other than hydrogen, then it is necessary to carry out the optional esterification of Step F. This esterification can be carried out using techniques well known in the art. Suitable esterification methods include refluxing the beta ketone phosphonate with an alcohol in the presence of an acid. This alcohol should correspond structurally to the desired ester moiety. Other methods known in the art may also be utilized.

Those compounds of Formula I in which R is represented by hydrogen and B is represented by an oxazolone:

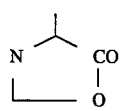

can also be made using techniques known in the art. These compounds can be produced using the same synthesis taught above in Reaction Scheme I, with the exception of one slight modification. The only modification is that in the deprotection reaction of Step E, the amount of TMSI that is utilized is changed. Approximately 3 equivalents of TMSI will produce a beta keto phosphonate as described by Formula I in which the benzyl carbamate protecting group and the alkyl groups represented by Y have been removed, but in which the oxazolone moiety is retained in the molecule.

Those compounds of Formula I in which B is represented by a piperazine moiety can also be prepared according to techniques known in the art. For example they can be prepared using the method taught below in Reaction Scheme III.

REACTION SCHEME III

STEP A

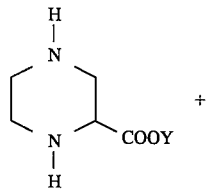

FORMULA VIII

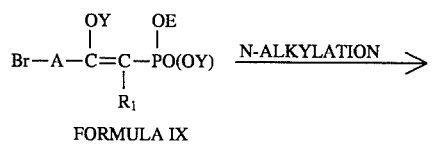

FORMULA IX

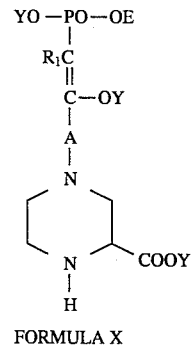

FORMULA X

STEP B

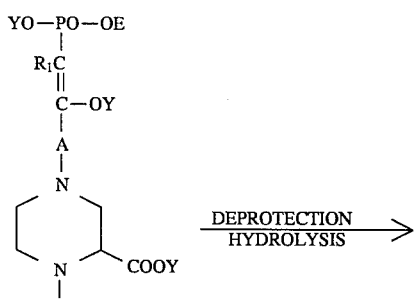

FORMULA X

-continued
REACTION SCHEME III

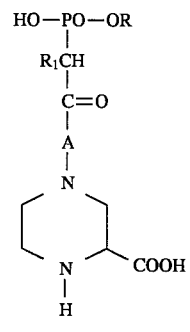

FORMULA I, Z = H

STEP C, OPTIONAL

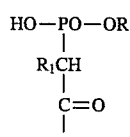

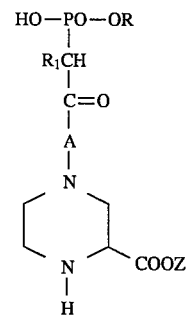

The first step of Reaction Scheme III is to conduct an N-alkylation between a piperazine derivative as described by Formula VIII in which Y is represented by a $C_{1-4}$ alkyl and a halo-enol phosphonate derivative as described by Formula IX in which $R_1$ and A are as in Formula I, E is a $C_{1-4}$ alkyl or $CF_3$ and each Y is independently represented by a $C_{1-4}$ alkyl. This N-alkylation produces the enol phosphonate derivative of Formula X in which Y, E, $R_1$ and A are as defined above. The enol phosphonate derivative of Formula X is then subjected to a hydrolysis reaction which serves to remove the protecting groups represented by Y and transforms the enol moiety into a carbonyl function. This hydrolysis can also remove the protecting group represented by E depending upon the concentration of acid that utilized. If R is to be represented by a hydrogen atom in the desired compound of Formula I, then this complete hydrolysis should be carried out. If Z is to be represented by an ester in the desired product of Formula I, then the optional esterification of Step C should be carried out.

One of the starting materials is a piperazine as described by Formula VIII in which Y is represented by a $C_{1-4}$ alkyl. This alkyl group will not be retained in the final product and thus its identity is immaterial. The other starting material is a halo-enol phosphonate as described by Formula IX in which each Y is independently represented by a $C_{1-4}$ alkyl, E is represented by a $C_{1-4}$ alkyl or $CF_3$ and $R_1$, and A are as in Formula I. The substituents represented by $R_1$, and A will be retained in the final product; therefore the halo-enol phosphonate that is utilized should have the same substituent at these positions as is desired in the final product of Formula I. The alkyl groups represented by Y will not be retained in the final product and their identity is immaterial. The substituent represented by E may be retained in the final product depending on whether a partial or complete hydrolysis is carried out. If E is to be represented by either $CF_3$ or a $C_{1-4}$ alkyl then the halo-enol phosphate utilized should contain this substituent at the E position. The piperazines of Formula VIII and the halo-enol phosphonates of Formula IX are known in the art as are their method of preparation.

The N-alkylation reaction can be carried out using techniques well known in the art. Typically approximately equimolar amounts of the piperazine derivative and the halo-enol phosphonate are contacted together in a polar solvent such as water, for a period of time ranging from about 0.5 to 18 hours. The N-alkylation is typically conducted at room temperature in the presence of a base such as sodium hydroxide. The base is typically present in the quantity of from about 1 to 3 equivalents. The enol piperazine derivative of Formula X produced thereby can be recovered from the reaction zone using techniques known in the art such as extraction or concentration. If desired, the enol piperazine derivative of Formula X can be purified by chromatographic techniques known in the art such as ion exchange chromatography.

The enol piperazine of Formula X is then subjected to a hydrolytic deprotection reaction which serves to remove the protecting groups represented by Y and may remove the protecting group represented by E depending upon reaction conditions. In order to remove both protecting groups represented by Y and E, the enol piperazine derivative of Formula X is contacted with about a 6 molar solution of a mineral acid such as hydrochloric acid. This hydrolysis is conducted at a temperature range of from about 60° C. to reflux for a period of time ranging from about 1 to 18 hours. Alternatively all of the protecting groups can be removed using TMSI in the manner taught in reaction Scheme I.

The partial hydrolysis in which E is not removed from the molecule is carried out by contacting the enol piperazine with a 1M molar solution of a mineral acid such as hydrochloric acid at a temperature range from 60° C. to reflux for a period of time ranging from one to eight hours. Regardless of which deprotection is utilized, the desired compound of Formula I can be recovered from the reaction by either concentration or extraction. It can then be purified by chromatographic techniques such as ion exchange chromatography or by recrystallization from a solvent system such as water and alcohol.

If Z is to be represented by an ester function, then it is necessary to carry out an esterification reaction in order to place the desired substituent on the Z position. This esterification can be conducted in the same manner as the esterification reaction of Step F in Reaction Scheme I. The esterified product can also be recovered and purified in the same manner as well.

Those compounds of Formula I in which B is represented by an α-substituted amino acid (ie. $H_2N$—CX—COOZ) can be prepared using the synthesis taught below in Reaction Scheme IV:

REACTION SCHEME IV

STEP A

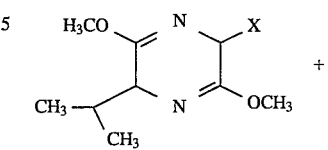

FORMULA XI

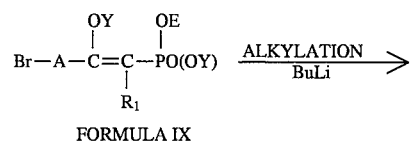

FORMULA IX

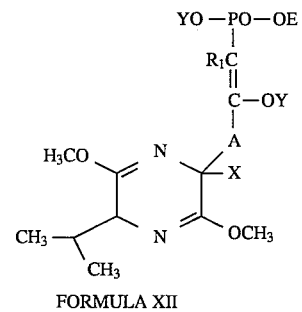

FORMULA XII

STEP B

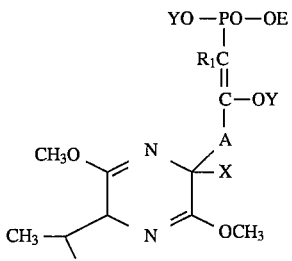

FORMULA XII

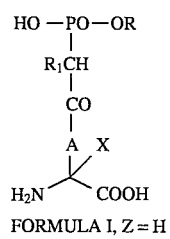

FORMULA I, Z = H

STEP C, OPTIONAL

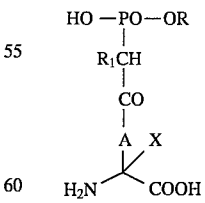

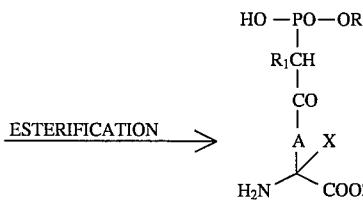

In Step A of Reaction Scheme IV, an alkylation reaction is conducted between a 3,6-dimethoxy-piperazine derivative as described by Formula XI in which X is as defined in Formula I and a halo-enol phosphonate derivative as previously described by Formula IX in which $R_1$ and A are as in Formula I, each Y is independently represented by a $C_{1-4}$ alkyl and E is a $C_{1-4}$ alkyl or $CF_3$. This alkylation produces the piperazine phosphonate derivative of Formula XII in which X, A, $R_1$, E and Y are as above. In Step B, the piperazine phosphonate derivative of Formula XII is subjected to a hydrolysis which cleaves the piperazine ring, removes the alkyl groups represented by Y, and may remove the substituent represented by E depending upon the manner in which the hydrolysis is carried out. This hydrolysis produces a beta-ketone phosphonate derivative as described by Formula I in which B is represented by an α-substituted amino acid (ie.$H_2N$—CX—COOZ). If Z is to be represented by an ester moiety, then it is necessary to carry out the esterification reaction of Step C.

The 3,6-dimethoxy-piperazine that is utilized as a starting material should have the same substituent at the X position as will be desired in the final product of Formula I. The halo-enol phosphonate of Formula IX that is utilized should have the same substituent at the A and $R_1$ position as is desired in the final product of Formula I. The alkyl substituents represented by Y will not be retained in the final product and their particular identity is not critical. If E is to be represented by either $CF_3$ or a $C_{1-4}$ alkyl then the halo-enol phosphate utilized should contain this substituent at the E position. The halo-enol phosphonates of Formula IX and the 3,6-dimethoxy piperazines of Formula XII are known in the art as are their method of preparation.

The alkylation reaction depicted in Step A can be carried out using techniques well known in the art. Typically, the 3,6-dimethoxy-piperazine is first contacted with an approximately equivalent amount of a base such as N-butyl lithium. They are typically contacted at a temperature range of from −78° C. to 0° C. for a period of time ranging from about 0.5 to 8 hours in a solvent such as tetrahydrofuran.

The reaction zone is then warmed to a temperature of about 30° C. and an approximately equimolar amount of the halo-enol phosphonate of Formula IX is added to the reaction. The reactants are then stirred together for a period of time ranging from about 1 to 18 hours. The reaction is then quenched with water and the piperazine phosphonate derivative of Formula XII is recovered from the reaction zone by either extraction or concentration. If desired, the piperazine phosphonate derivative of Formula XII can be purified by chromatographic techniques known in the art such as flash chromatography or by recrystallization from a solvent system such as ethyl acetate/hexane as is known in the art.

The next step in the reaction sequence is to subject the piperazine phosphonate derivative of Formula XII to the hydrolysis depicted in Step B. This hydrolysis reaction can be carried out using techniques known in the art. If a complete hydrolysis is desired, (ie. R is to be H) then the piperazine phosphonate is contacted with a 0.25 to 6 molar solution of a mineral acid such as HCL. The deprotection reaction is typically carried out at a temperature range of from about 20° to 100° C. for a period of time ranging from 1 to 18 hours.

If a partial hydrolysis is desired, (ie. the substituent represented by E is to be retained in the final product) then the hydrolysis is carried out for 1 to 2 hours with a 0.2 to 1M solution of HCl. The resulting beta ketone phosphonate of Formula I produced via either hydrolysis can be recovered from the reaction zone by either concentration or extraction. The beta ketone phosphonate of Formula I can then be purified in the manner taught in Step B of Reaction Scheme III.

As in the other Reaction Schemes, if Z is to be represented by an ester function then it is necessary to carry out the esterification reaction depicted in Step C.

Those compounds of Formula I which R is a non-hydrogen substituent and B is an amino acid or a derivative of an amino acid, (ie. $H_2N$—CH—COOZ) can also be prepared using the methods taught immediately above in Reaction Scheme IV. The only modification to the reaction sequence is in the starting materials that are utilized. The 3,6-dimethoxy piperazine of Formula XII that is utilized should have a hydrogen atom at the X-position. Since R will be a non-hydrogen substituent, the deprotection reaction of Step B should be a partial hydrolysis.

Those compounds of Formula I in which B is represented by an α-substituted amino acid can also be prepared by carrying out an alkylation reaction between a halo-enol phosphonate as previously described by Formula IX and an imine as described by Formula XIII in below in which X is as defined in Formula I, Ph represents a phenyl ring, and Alk represents a $C_{1-4}$ alkyl:

FORMULA XIII

This alkylation reaction can be conducted in the same manner as the alkylation reaction depicted in Step A of Reaction Scheme IV. This alkylation produces an imine phosphonate as described by Formula XIV below in which $R_1$, X and A are as defined in Formula I, and Ph and Alk are as defined above:

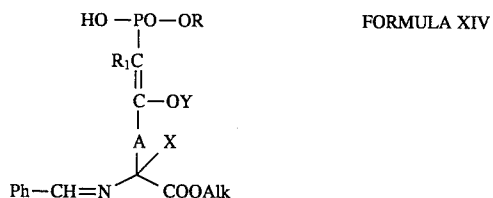

FORMULA XIV

A beta ketone phosphonate of Formula I can then be produced by subjecting the imine phosphonate of Formula XIV to an acidic hydrolysis in the same manner as the deprotection reaction of Step B in Reaction Scheme IV. As in the other reaction Schemes, if Z is to be represented by an ester moiety, then an esterification reaction needs to be conducted. This esterification reaction can be conducted in the same manner as the esterification reaction in Step F of Reaction Scheme I.

The compounds of Formula Ia can also be prepared utilizing techniques known in the art. One method for preparing these compounds is disclosed below in Reaction Scheme V:

REACTION SCHEME V

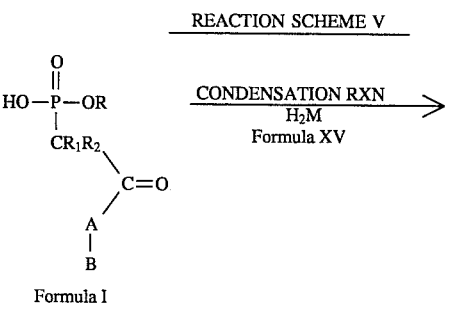

-continued
REACTION SCHEME V

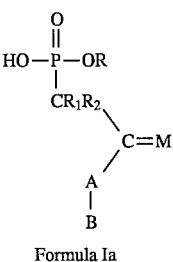

Formula Ia

In Reaction Scheme V, one of the beta ketone phosphonates of Formula I is subjected to a condensation reaction with either an oxime or hydrazine derivative, as depicted by Formula XV in which M is as defined in Formula Ia. This produces one of the beta hydrazones or beta oximes of Formula Ia.

The appropriate reactants for the condensation reaction are a beta ketone phosphonate in which A, B, $R_1$, $R_2$ and R are represented by the same substituent as is desired in the final product and an appropriately substitued oxime or hydrazine in which M is represented by the same substituent as is desired in the final product. The condensation reaction can be carried out using techniques known in the art. Typically approximately equivalent amounts of the compound of Formula XV and the beta ketone phosphonate of Formula I are contacted in a buffered solution. Sodium acetate is one suitable buffer. The reaction is typically carried out at a temperature range of from 25° to 80° C. for a period of time ranging from 1 to 24 h. The desired compound of Formula Ia can then be recovered from the reaction and purified by either gel filtration or ion exchange chromatography.

The compounds of Formulae I and Ia are excitatory amino acid antagonists. They antagonize the effects which excitatory amino acids have upon the NMDA receptor complex. They preferentially bind to the glutamate binding site located on the NMDA receptor complex. They are useful in the treatment of a number of disease states.

The compounds exhibit anti-convulsant properties and are useful in the treatment of epilepsy. They are useful in the treatment of grand mal seizures, petit mal seizures, psychomotor seizures, and autonomic seizures. One method of demonstrating their anti-epileptic properties is by the compounds ability to inhibit audiogenic convulsions in DBA/2 mice. This test can be conducted in the following manner.

Typically one group of from 6–8 male DBA/2J audiogenic susceptible mice are administered from about 0.01 µg to about 100 µg of the test compound. The test compound is administered intracerebrally into the lateral ventricle of the brain. A second group of mice are administered an equal volume of a saline control by the same route. Five minutes later the mice are placed individually in glass jars and are exposed to a sound stimulus of 110 decibels for 30 seconds. Each mouse is observed during the sound exposure for signs of seizure activity. The control group will have a statistically higher incidence of seizures than the group which receives the test compound.

Another method for demonstrating the anti-epileptic properties of these compounds is by their ability to inhibit the seizures that are caused by the administration of quinolinic acid. This test can be conducted in the following manner.

One group containing ten mice are administered 0.01–100 ug of test compound intracerebroventricularly in a volume of 5 microliter of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic seizures. The control group will have a statistically higher rate of clonic seizures than will the test group.

The compounds of Formulae I and Ia are useful for preventing or minimizing the damage which nervous tissues contained within the CNS suffer upon exposure to either ischemic, hypoxic, or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. These anxiolytic properties can be demonstrated by their ability to block distress vocalizations in rat pups. This test is based upon the phenomenon that when a rat pup is removed from its litter, it will emit an ultrasonic vocalization. it was discovered that anxiolytic agents block these vocalizations. The testing methods have been described by Gardner, C. R., Distress vocalization in rat pups: a simple screening method for anxiolytic drugs. *J. Pharmacol. Methods*, 14: 181–187 (1985) and Insel et al., Rat pup ultrasonic isolation calls: Possible mediation by the benzodiapine receptor complex, *Pharmacol. Biochem. Behav.*, 24: 1263–1267 (1986). The compounds also exhibit an analgesic effect and are useful in controlling pain.

The compounds of Formula I and Ia are muscle relaxants and are therefore useful for releiving muscle spasms. One method of demonstrating their utility as muscle relaxants is via the Straub Tail test. This screening procedure is based upon the observation that the administration of morphine to mice produces a sustained contraction of their sacrococcygeus muscle which causes their tail to be elevated at an angle of approximately 90°. A muscle relaxant prevents contraction of this muscle and inhibits tail elevation. These tests have been described by K. O. Ellis, et al., *Neuropharmacology*, Vol. 13, pp. 211–214 (1974).

In order to exhibit any of these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 1 mg/kg/day to about 500 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formulae I and Ia can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

As used in this application:

a) the term patient refers to warm blooded animals such as, for example, guinea pigs, mice, rats, cats, rabbits, dogs, monkeys, chimpanzees, and humans;

b) the term treat refers to the ability of the compounds to either relieve, alleviate, or slow the progression of the patient's disease;

c) the term neurodegeneration refers to a progressive death and disappearance of a population of nerve cells occurring in a manner characteristic of a particular disease state and leading to brain damage.

The compounds may also be admixed with any inert carrier and utilized in laboratory assays in order to determine the concentration of the compounds within the serum, urine, etc., of the patient as is known in the art.

Neurodegenerative diseases are typically associated with a loss of NMDA receptors. Thus, the compounds of Formulae I and Ia may be utilized in diagnostic procedures to aid physicians with the diagnosis of neurodegenerative diseases.

The compounds may be labeled with isotopic agents by techniques known in the art and utilized as imaging agents. They may then be administered to a patient in order to determine whether the patient is exhibiting a decreased number of NMDA receptors and the rate at which that loss is occurring.

The following examples are presented in order to further illustrate the invention. They should not be construed as limiting the invention in any manner.

EXAMPLE I

The purpose of this Example is to demonstrate the preparation of the protected amino acids of Formula III using the methods disclosed in Step A of Reaction Scheme I and Method of V. J. Lee & K. L. Rinehart J. Am. Chem. Soc. 1978, 100, 4237.

A) N-Benzyloxycarbonyl-D-aspartic Acid

D-Aspartic acid (25.0 g, 0.188 mol) and benzyl chloroformate (34.3 ml, 0.282 mol) were added to sodium hydroxide (22.9 g, 0.564 mol) in water (600 ml). The resulting mixture was stirred at room temperature for 3 days. The mixture was then acidified with 6MHCl to pH1 and extracted with ethyl acetate (3×250 ml). The extracts were combined, dried ($MgSO_4$) and evaporated to a clear oil, wt 50.2 g. $^1H$ NMR (90 $MH_z$, $CDCl_3$): δ3.05 (2,bm), 4.65 (1,bm), 5.25 (2,s), 6.2 (1,bs), 7.4 (5,s), 10 (1,bs).

B) N-Benzyloxycarbonyl-3-methyl-D,L-aspartic Acid

Using a similar method to above 3-methyl-D,L-aspartic acid (10.0 g, 67 mmol), benzyl chloroformate (12 ml, 100 mmol) in 50% NaOH (16.7 g, 208 mmol) in water (125 ml) yielded N-benzyloxycarbonyl-3-methyl-D,L-aspartic acid 19.0 g as a low melting solid. $^1H$ NMR (90 $MH_z$, $CDCl_3$/$d_6DMSO$): δ1.1 (3,d), 2.9 (1,dt), 4.4 (1,m), 4.95 (2,s) 5.9 (1,bd) 7.2 (5,6) 7.9 (1,bs).

C) N-Benzoylcarbonyl-D-2-Aminoadipic Acid

Using a similar method to above D-2-amino-adipic acid (4.0 g, 24.8 mmol), benzyl chloroformate (4.5 ml, 37.2 mmol) and 50% sodium hydroxide (6.0 g, 74.4 mmol) in water yielded N-benzoylcarbonyl-D-2-amino adipic acid 7.5 g as a low melting solid. $^1H$ NMR (300 $MH_z$, $CDCl_3$) δ1.65 (2,m) 1.78 (2,m) 2.41 (2,t) 3.8 (1,t) 5.1 (2,s) 7.4 (5,m).

EXAMPLE II

The purpose of this Example is to demonstrate the preparation of the oxazolone derivatives of Formula IV by the method disclosed in Step B of Reaction Scheme I and Method of M.ITOH Chem. Pharm. Bull. 1969, 17, 1679.

A) R-5-Oxo-4-acetic-3-oxazolidinecarboxylic acid, 3-(phenylmethyl) ester

N-Benzyloxy carbonyl-D-aspartic acid (52 g, 195 mmol) was added to para-formaldehyde (16 g) and para-toluene sulphonic acid (1 g) in benzene (1 L). The resolving mixture was heated to the boil and refluxed for 4½ hours with azaetropic removal of water (Dean & Starke trap). The mixture was then cooled and poured into 1MHCl (500 ml). The resulting mixture was extracted with ethyl acetate (3×250 ml) and the extracts combined and washed with 5% sodium bicarbonate (2×500 ml). The bicarbonate extracts were combined, acidified with 6MHCl then extracted with ethyl acetate (3×250 ml). The ethyl acetate extracts were combined, dried ($MgSO_4$) and evaporated to a low melting white solid, wt 25.9 g. $^1H$ NMR (90 $MH_z$, $CDCl_3$) δ3.05 (2,m) 4.25 (1,t), 5.05 (2,s), 5.25 (2,dd), 7.2 (5,s), 7.5 (1,bs).

B) S-5-Oxo-4-acetic-3-oxazolidinecarboxylic acid, 3 (phenylmethyl)ester

Using a similar method to above N-benzyloxycarbonyl-L-aspartic acid (10 g, 37 mmol), para-formaldehyde (3 g) and para-toluenesulphonic acid (0.25 g) in benzene (250 ml) yielded 10.1 g of a low melting solid. $^1$H NMR (90 MH$_z$, CDC$_3$) δ3.05 (2,m), 4.25 (1,t) 5.05 (2,s) 5.25 (2,dd) 7.2 (5,s), 7.5 (1,bs).

C) R,S-5-Oxo-4-(α-methyl acetic acid)-3-oxazolidine carboxylic acid, 3-pheny(methyl)ester Using a similar method to above N-benzyloxycarbonyl-3-methyl-D,L-aspartic acid (18.8 g, 67 mmol), para-formaldehyde (6 g) and para-toluenesulphonic acid (0.5 g) in benzene (500 ml) yielded 13.5 g of a low melting solid. $^1$H NMR (90 MH$_z$, CDCl$_3$) δ1.5 (3,d) 3.25 (1,m) 4.2 (1,D) 5.2 (2,s) 5.35 (2,dd), 7.2 (5,6), 9.2 (1,bs).

D) R-5-Oxo-4-butyric-3-oxazolidinecarboxylic acid, 3-(phenymethyl)ester

Using a similar method to above N-benzyloxycarbonyl-D-2-aminoadipic acid (7.5 g, 24.8 mmol), paraformaldehyde (5 g) and paratoluene sulphonic acid (0.5 g) in benzene yielded 5.83 g of a clear oil. $^1$H NMR (90 MH$_z$,CDCl$_3$) δ1.7 (2,m) 1.95 (2,m) 2.35 (2,m) 4.3 (1,m) 5.2 (2,s) 5.35 (2,dd) 7.4 (5,s).

EXAMPLE III

The purpose of this Example is to demonstrate the preparation of the acid chlorides of Formula V by the methods taught in Step C of Reaction Scheme I and Method of B. H. Lee & M. J. Miller Tetrahadron Lett. 1984, 25,927.

A) R-5-Oxo-4-(acetyl chloride)-3-oxazolidinecarboxylic acid, 3-(phenylmethyl)ester Thionyl chloride (20 ml) was added to R-5-oxo-4-acetic-3-oxazolidinecarboxylic acid, 3-(phenylmethyl)ester (9.8 g, 35.1 mmol) and refluxed for 10 minutes. The solution was then cooled and blown to a residue with a stream of dry N$_2$. The residue was then concentrated under vacuum to yield a pale yellow oil (10.4 g). $^1$H NMR (90 MH$_z$, CDCl$_3$) δ3.5 (2,d) 4.2 δ (1,t) 5.1 (2,s) 5.25 (1,dd) 7.2 (5,s).

B) S-5-Oxo-4-(acetyl chloride)-3-oxazolidine carboxylic acid, 3-(phenylmethyl)ester Using a similar method to above thionyl chloride (18 ml) and S-5-oxo-4-acetic-3-oxazolidine carboxylic acid, 3-(phenyl methyl)ester (10.1 g, 36 mmol) yielded 10.8 g of a yellow oil.

C) R,S-5-Oxo-4-(α-methyl-acetyl chloride)-3-oxazolidine carboxylic acid, 3-(phenylmethyl)ester Using a similar method to above thionyl chloride (15 ml) and R,S-5-oxo-4-(α-methyl acetyl chloride)-3-oxazolidine carboxylic acid, 3-(phenylmethyl)ester yielded 7.4 g of a straw colored oil.

D) R-5-Oxo-4-(butryl chloride)-3-oxazolidine carboxylic acid, 3-(phenylmethyl)ester Using a similar method to above thionyl chloride (8 ml) and R-5-oxo-4-butyric-3-oxazolidine carboxylic acid, 3-(phenylmethyl)ester (5.8 g, 18.9 mmol) yielded 6.1 g of a colorless oil.

EXAMPLE IV

The purpose of this Example is to demonstrate the preparation of the protected beta Ketone phosphonates of Formula VII utilizing the coupling techniques taught in Step D of Reaction Scheme I and Method of J. M. Vaslet, N. Collignon & P. Savignac Can J. Chem. 1979, 57, 3216.

A) R-4-[3-(Diethoxyphosphinyl)-2-oxopropyl]-5-oxo-3-oxazolidine carboxylic acid, 3-(phenylmethyl)ester Diethyl methylphosphonate (25.1 g, 165 mmol) was dissolved in THF (250 ml) under N$_2$ and cooled to −65° C. 2.7 M $^n$BuLi (61 ml, 165 mmol) in hexanes was added dropwise over 15 minutes to the solution and stirred for a further 10 minutes while maintaining a temperature of −65°. Copper I iodide (34.7 g, 182 mmol) was added and the resulting mixture warmed to −30° C. and then stirred for an additional 1 h. R-5-Oxo-4-(acetyl chloride)-3-oxazolidine carboxylic acid, 3-(phenylmethyl)ester (54.2 g, 182 mmol) in ether (250 ml) was then added dropwise so as to maintain a temperature of −30° C. and the resulting mixture stirred for a further 18 hours. The reaction was then poured into water (750 ml) and the aqueous mixture then extracted with dichloromethane (3×250 ml). The organic extracts were then combined, filtered through a bad of celite, dried (MgSO$_4$) and evaporated to a pale yellow oil. Flash chromatography on silica gel with 100% ethyl acetate yielded a colorless oil wt. 31.9 g. $^1$H NMR (300 MH$_z$, CDCl$_3$) δ1.24 (6,t) 2.95 (2,d) 3.32 (2,m) 3.98 (4,m), 4.15 (1,m) 5.1 (2,s) 5.35 (2,dd) 7.28 (5,5); MS (CI), M/Z 414 (MH+).

B) S-4-[3-(Diethyoxyphosphinyl)-2-oxopropyl]-5-oxo-3-oxazolidine carboxylic acid, 3-(phenylmethyl)ester Using a similar method to above, S-5-oxo-4-(acetyl chloride)-3-oxazolidinecarboxylic acid, 3-(phenylmethyl)ester (10.8 g, 36.3 mmol), methyl diethyl phosphonate (5.0 g, 33 mmol), 2.7M $^n$BuLi (12.2 ml, 33 mmol) and copper I iodide (6.91 g, 36.3 mmol) in THF (50 ml) and ether (50 ml) yielded a colorless oil wt 5.0 g $^1$H NMR (300 MH$_z$, CDCl$_3$) δ1.25 (6,t) 2.95 (2,d) 3.32 (2,m) 3.98 (4,m) 4.15 (1,m) 5.1 (2,s) 5.35 (2,dd) 7.28 (5,s); Ms (CI), M/Z 414 (MH+).

C) 4-[3-(Diethoxyphosphinyl)-1-methyl-2-oxopropyl]-5-oxo-3-diethyl phosphonate)-3-oxazolidine carboxylic acid, 3-(phenyl methyl)ester Using a similar method to above, 5-oxo-4-(α-methyl acetyl chloride)-3-oxazolidine carboxylic acid, 3-(phenyl methyl)ester (7.4 g, 23.7 mmol), diethyl methyl phosphonate (3.28 g, 21.5 mmol), 2.7M $^n$BuLi (8.0 ml, 21.5 mmol) and copper I iodide (4.5 g, 23.7 mmol) in THF (40 ml) and ether (40 ml) yielded 3.17 g of a colorless oil. $^1$H NMR (90 MH$_z$, CDCl$_3$) δ1.2 (6,t) 1.4 (3,d) 2.95 (2,d) 4.1 (4,m) 5.1 (2,s) 5.25 (2,dd) 7.25 (5,s) MS CCZ), M/Z 428 (MH+).

D) 4-[3-(Diethoxyphosphinyl)-1,3-dimethyl-2-oxopropyl]]-5-oxo-3-oxazolidinecarboxylic acid, 3-(phenylmethyl)ester Using a similar method to above, 5-oxo-4-(α-methyl acetyl chloride)-3-oxazolidine carboxylic acid, 3-(phenyl methyl ester (6.9 g, 22 mmol), diethyl ethyl phosphonate (3.32 g, 20 mmol) and copper I iodide (4.19 g, 22 mmol) in THF (50 ml) and ether (50 m) yielded 2.1 g of a colorless oil. $^1$H NMR (300 MH$_z$, CDCl$_3$) 1.1 (6,m) 1.12 (3,m) 1.96 (3,m) 3.4 (1,m) 3.6 (1,m) 4.25 (1,m) 5.2 (2,s) 5.35 (2,dd) 7.4 (5,s). MS (CI) M/Z 442 (MH+).

E) R-4-[3-(Diethoxyphosphinyl)-3-methyl-2-oxopropyl]-5-oxo-3-oxazolidine carboxylic acid, 3-(phenylmethyl)ester Using a similar method to above R-5-oxo-4-(acetyl chloride)-3-oxazolidinecarboxylic acid, 3-(phenylmethyl)ester (4.79 g, 16.1 mmol), ethyl diethyl phosphonate (2.43 g, 14.6 mmol), 2.7M $^n$BuLi (5.40 ml, 14.6 mmol) and copper I iodide (31 g, 16.1 mmol ) in THF (30 ml) and ether (40 ml) yielded 2.1 g of a clear oil. $^1$H NMR (90 MH$_2$, CDCl$_3$) 1.2 (6,m) 1.25 (3,s) 3.1 (1,m) 3.8 (1,m) 4.05 (4,m) 5.1 (2,s) 5.25 (2,dd) 7.2 (5,s) MS CI M/Z 428 (MH+).

F) R-4-[5-(Diethoxyphosphinyl)-4-oxopentyl]-5-oxo-3-oxazolidine carboxylic acid, 3-(phenyl methyl)ester Using a similar method to above R-5-oxo-4-(butryl chloride)-3-oxazolidinecarboxylic acid, 3-(phenyl methyl)ester (6.1 g, 18.7 mmol), methyl diethyl phosphonate (2.6 g, 17 mmol), 2.7M $^n$BuLi (6.3 ml, 17 mmol) and copper I iodide (3.6 g, 18.7 mmol) in THF (50 ml) and either (50 ml) yielded a clear oil, wt. 2.5 1 g. $^1$H NMR (300 MH$_z$, CDCl$_3$) δ1.32 (6,t) 1.59 (2,m) 1.80 (1,m) 1.99 (1,m) 2.61 (2,m) 3.04 (2,d) 4.13 (4,m) 4.35 (1,m) 5.2 (2,s) 5.35 (2,dd) 7.4 (5,s).

EXAMPLE V

The purpose of this Example is to demonstrate the preparation of the beta ketone phosphonates of Formula I via the methods taught in Step E of Reaction Scheme I.

A) R-4-oxo-5-phosphononorvaline

R-4-[3-(Diethoxyphosphinyl)-2-oxopropyl]-5-oxo-3-oxazolidinecarboxylic acid, 3-(phenylmethyl)ester (20.0 g, 48 mmol) was dissolved in CH$_2$Cl$_2$ (750 ml) and acetonitrile (750 ml) and cooled under an atmosphere of dry N$_2$ to 0° C. Trimethyl silyl iodide (27.6 ml, 20.1 mmol) was added dropwise over 10 minutes and the resulting solution warmed to room temperature and stirred for 4½ hours. Water (20 ml) was than added and the reaction blown to a residue with a stream of N$_2$. The residue was taken up in CH$_2$Cl$_2$ (250 ml) and water (200 ml). The aqueous layer was then washed with CH$_2$Cl$_2$ (10×20 ml) then washed with diethyl ether (3×300 ml) and then lyophilized to yield a yellow powder. The powder was taken up into a minimum volume of water and eluted on a BIORAD AG5OW-X8 H+ form resin with water. The ninhydrin positive fractions were lyophylized to yield 6.2 g of an off white solid. The solid was taken back up in a minimum amount of water and reluted through a BIORAD Ag5OW-X4 H+ form resin with water yielded 4.8 g of a white solid MP 154° (with decomposition). $^1$H NMR (300 MH$_z$, D2O) 3.05 (2,dd) 3.35 (2,m) 4.2 (1,m); $^{31}$PNMR (121 MH$_z$, D$_2$O) 12.4 (s); MS (FAB) M/Z 212 (MH+) Anal. Calcd. for C$_5$H$_{10}$NO$_6$P ½ H$_2$O: C,27.28; H, 5.04; N, 6.45. Found: C, 27.27; H, 4.82; N, 6.35. Weight loss by thermo gravimetry correlates with 4.8 wt. % water.

B) S-4-oxo-5-phosphononorvaline

Using a similar method to above S-4-[3-(Diethoxyphosphinyl)-2-oxopropyl]-5-oxo-3-oxazolidinecarboxylic acid, 3-(phenyl methyl)ester (5.0 g, 12 mmol) and trimethylsilyl iodide (6.9 ml, 48 mmol) in dichloromethane (250 ml) and acetonitrile (300 ml) to yield 0.28 g of a white solid. Mp 155° C. (with decomposition). $^1$H NMR (300 MH$_z$, D$_2$O) 3.05 (2,dd) 3.35 (2,m) 4.2 (1,m); $^{31}$PNMR (121 MH$_z$, D$_2$O) 12.4 M S (FAB) m/z 212 (MH+). Anal. Calcd. for C$_5$H$_{10}$NO$_6$P ½ H20: C,27.28; H,5.04, N, 6.45. Found C, 27.07; H, 4.98; N, 6.37. Weight loss by thermo gravimetry correlates with 3.9 wt. % water.

C) 3,4-dimethyl-4-oxo-5-phosphononorvaline

Using a similar method to above 4-[3-(Diethoxyphosphinyl)-1,3-dimethyl-2-oxopropyl]-5-oxo-3-oxazolidine carboxylic acid, 3-(phenylmethyl)ester (2.0 g, 4.5 mmol) and trimethyl silyiodide (2.6 ml, 18.1 mmol) in dichloromethane (100 ml) and acetonitrile (100 ml) yielded 21.4 mg of white solid m.p. 72° with decomposition. $^1$H NMR 1.25 (6,m), 2.49 (1,m), 4.22 (1,m); $^{31}$PNMR (121 MH$_z$, D$_2$O) 16.1 (s); Ms (FAB) m/z 240 (MH+). Anal. Calcd. for C$_7$H$_{14}$NO$_6$P ½H$_2$O: C,35.15; H,5.90; N,5.86 Found: C,34.13; H,5.16, N, 5.22. Weight loss by thermo gravimetry correlates with 7.3% wt. % water.

D) 3-methyl-4-oxo-5-phosphononorvaline

Using a similar method to above 4-[3-(Diethoxyphosphinyl)-1-methyl-2-oxopropyl]-5-oxo-3-oxazolidine carboxylic acid, 3(phenylmethyl)ester (3.17 g, 7.4 mmol) and trimethylsilyl iodide (4.3 ml, 30.2 mmol) in dichloromethane (200 ml) and acetonitrile (200 ml) yielded 310 mg of a white solid m.p. 145° (with decomposition). $^1$H NMR (300 MH$_z$, D$_2$O) δ1.35 (3,d) 3.21 (2,dd) 3.61 (6,m) 4.35 (1,m); $^{31}$PNMR (121 MH$_z$, D$_2$O) 11.90; (MS FAB) 226 (MH+). Anal. calcd. for C$_6$H$_{12}$NO$_6$ P ½ H$_2$O: C,30.78; H, 5.60; N, 5.98. Found: C, 30.90; H, 5.48, N, 5.93. Weight loss by thermo gravimetric correlates with 4.3 wt. % water.

E) R-5-methyl-4-oxo-5-phosphononorvaline

Using a similar method to above R-413-Diethoxyphosphinyl)-3-methyl-2-oxopropyl]-5-oxo-3-oxazolidine carboxylic acid, 3-(phenyl methyl)ester (2.1 g, 4.9 mmol) and trimethylsilyl iodide (2.9 ml, 20.4 mmol) in dichloro-methane (150 ml) and acetonitrile (150 ml) yielded 70 mg of white solid m.p. 140° (with decomposition). $^1$H NMR (300 MH$_2$, D$_2$O) 1.35 (3,m) 3.31 (2,m) 3.54 (1,m) 4.28 (1,m) $^{31}$P NMR (121MH$_2$, D$_2$O) δ16.3 (s); M S (FAB) M/Z 226 (MH+) Anal. calcd for C$_6$H$_{12}$ NO$_6$ P ½ H$_2$O: C, 30.78; H, 5.60; N, 5.98. Found: C, 30.45, H, 5.24; N, 5.86. Weight loss by thermo gravimetry correlates with 5.2 mol % water.

F) R-2-Amino-6-oxo-7-phosphonoheptanoic acid

Using a similar method to above R-4-[5-(Diethoxyphosphinyl)-4-oxopentyl]-5-oxo-3-oxazolidine carboxylic acid, 3-(phenyl methyl)ester (2.5 g, 5.7 mmol) and trimethyl-silyl iodide (3.2 ml, 22.8 mmol) in dichloromethane (150 ml) and acetonitrile (150 ml) yielded 400 mg of a white solid m.p. 82° with decomposition. $^1$H NMR (300 MH$_z$, d$_6$DMSO) 1.65 (2,m) 1.90 (2,m) 2.8 (2,m) 3.1 (2,D) 4.4 Cl,M); $^{31}$P NMR (121 MH$_z$, D$_2$O) 9.3 (s); M S (FAB) 240 (MH+). Anal calcd. for C$_7$ H$_{14}$ NO$_6$P. C, 35.15; H, 5.90; N, 5.86. Found: C, 35.38; H, 5.60, N, 5.80.

EXAMPLE VI

The purpose of this Example is to demonstrate the preparation of a beta ketone phosphonate of Formula I in which B is represented by a piperazine derivative using the methods taught in Reaction Scheme III.

4-(2-Oxo-3-phosphonopropyl)-2-piperazinecarboxylic acid

Piperazine-2-carboxylic acid hydrochloride 1.2 g (7.2 mmol) was dissolved in water (25 ml) and 80% sodium hydroxide (1.4 g), and dimethyl-1-bromo-2-methoxy propenyl phosphonate (2.4 g, 9.3 mmol) added. The resulting solution was stirred for 18 hours under a N$_2$ atmosphere, then acidified to pH 3.0 with 1MHCl. The reaction was blown to a residue with a stream of N$_2$ and then taken up in a minimum amount of water and eluted from a BIORAD Agl-X8 acetate form in resin with water. The ninhydrin positive fractions were lyophylized and hydrolysed with refluxing 6MHCl (50 ml) for 6 hours. The reaction was blown to a residue and eluted from a Amberlite CG-50 ion-exchange resin with water hyphoylization yielded 71 mg of a white solid. $^1$H NMR (300 MH$_z$, D$_2$O) δ3.02 (2,d) 3.3–3.6 (3,m) 3.6–3.8 (2,m) 3.7 (1,m) 3.71 (2,m). $^{31}$PNMR (121 MH$_z$, D$_2$O) 12.25.

EXAMPLE VII

The purpose of this Example is to demonstrate the preparation of all of the beta-substituted beta ketone phosphonates at Formula I using the method disclosed in U. Schollkopf, V. Groth, K.-O. Westphalen And C. Deng, *Synthesis* 1981, 969. Synthesis of 2-methyl-4-oxo-5-phosphononorvaline D,L-Alanine ethyl ester hydrochloride (10.0 g; 65.1 mmol) was added to benzaldehyde (6.6 ml; 65.1 mmol), magnesium sulfate (6 g) and triethylamine (20 ml) in dichloromethane (50 ml) and stirred at room temperature for 18 hours. The solids were filtered off and the filtrate partioned between ether (250 ml) and water (250 ml). The organic layer was separated, dried and evaporated to yield a clear oil wt 11.3 g. $^1$H NMR (90 MH$_z$, CDCl$_3$) δ1.2 (3,t) 1.4 (3,d) 4.0 (1,m) 4.1 (2,q) 7.4 (5,m) 8.2 (1,s).

The oil (2.62 g; 12.8 mmol) was added to THF (200 ml) and cooled to −78° for ½ hour. Lithium hexamethylsilylamine (1.0M in hexane; 12.8 mmol was added and stirred for ½ hour. Dimethyl-3-bromo-2-methoxy propenyl phosphonate (3.3 g, 12.8 mmol) in THF (75 ml) was added dropwise over ½ hour and the resulting solution stirred and warmed to room temperature over 18 hours. The reaction was then poured into water (500 m) and extracted with ethyl acetate (2×500 ml). The organic extracts were combined dried ($MgSO_4$) and evaporated to a residue which was flash chromatographed on silica gel with ethyl acetate to yield 1.8 g of a clear oil. $^1H$ NMR (300 $MH_z$, $CDCl_3$) 1.23 (3,6) 1.49 (3, s) 3.3–3.8 (11,m) 4.19 (1,q) 4.49 (1,D) 7.5 (m,5) 8.32 (1,s).

6MHCl (400 ml) was added to the oil (1.8 g, 4.6 mmol) and the mixture heated to the boil and refluxed under an atmosphere of $N_2$ for 6 hours. The solution was then evaporated to a residue. The residue was taken up in ethanol (10 ml) and isopropyl alcohol (3 ml) and propylene oxide (1 ml) added. The resulting solid was filtered and dried wt. 0.75 g, m.p. 130° with decomposition. $^1H$ NMR (300 $MH_z$, $D_2O$) 1.55 (3,s) 3.05 (1,ddd) 3.45 (1,dd); MS (FAB) M/Z 226 (MH+).

EXAMPLE VIII

The purpose of this Example is to demonstrate a partial hydrolysis in which the phosphonate ester moiety is retained in the final product.

5-(Hydroxymethoxyphosphinyl)-4-oxonorvaline

N-(Diphenylmethylene)glycine ethyl ester (3.1 g, 11.6 mmol) was dissolved in THF (50 ml) and cooled to −78° under a dry atmosphere of $N_2$. 1M Lithium hexamethylsilyamine in hexanes (12 ml, 12 mmol) was added and the resulting orange solution stirred at −78° for ½ hour. Dimethyl-3-bromo-2-methoxypropenyl phosphate (3 g, 12 mmol) was added and the solution stirred and allowed to warm to room temperature over 18 hours. The reaction was then poured into water (200 ml) and extracted with ethyl acetate (2×250 ml). The organic extracts were combined, dried ($MgSO_4$) and evaporated to a residue. Flash chromatography on silica gel with ethyl acetate, hexane (75:25) yielded 3.2 g of a light yellow oil. 1MHCl (50 ml) was added to the oil (2.63 g); 5.9 mmol) and refluxed for 1½ hours. The resulting solution was evaporated to a residue and eluted with water on a BIORAD 50W:X8H+ resin with water to yield 0.65 g of a white solid Mp 111° (with decomposition). $^1H$ NMR (300 $MH_z$, $D_2O$) δ3.15 (1,d) 3.45 (1,m) 3.61 (3,d) 4.31 (1,m); MS (FAB) M/Z 226 (MH+) Anal. Calcd. for $C_6H_{12}NO_6$ P ½$H_2O$; C, 30.78; H, 5.60, N, 5.98. Found: C, 31.11; H, 5.57; N, 6.07.

EXAMPLE IX

This example demonstrates the preparation of the oximes of Formula Ia.

A) 4-(Hydroxyimino)-5-phosphonorvaline 0.25 g of R-4-Oxo-5-phosphononorvaline (1.1 mmol) were stirred at 40° C. with 1.0 g sodium acetate (12.2 mmol) and 0.50 g hydroxylamine.HCl (7.2 mmol) in 5 ml water. Disappearance of starting material by HPLC indicated completion of the reaction. The reaction mixture was eluted through a column of Sephadex® G-10 with D.I. water. The ninhydrin positive fractions were then combined and condensed by freeze drying to yield 153 mg (59%) of 4-(hydroxyimino)-5-phosphononorvaline as white hygroscopic solid, m.p. 128° C. (with decomposition). Calculated as anhydrous: C, 26.56; H, 4.90; N, 12.39. Found: C, 21.13; H, 4.45, N, 9.85. TGA: 9.7% loss. FAB MS M+H 227.1; 300 MHz NMR in $D_2O$ $^1H$: 4.25 M, 4.15 M (total 1 H) 30 M(2H), 3.1 M(2H) $^{31}P$(1H decoupled): 14.8, 15.75; $^{13}C$: 32–34 D, 38, 55, 157D, 177.

B) 4-(Methoxyimino)-5,phosphononorvaline 0.21 g of R-4-Oxo-5-phosphononorvaline and 0.5 g of O-methyl hydroxylamine.HCl, were reacted as in Example IX(A) and 4-(methoxyimino)-5-phosphononorvaline was obtained as a white hygroscopic solid, m.p. 170° C. (with decomposition). (52%) Calcd: C, 30.01; H, 5.46; N, 11.67. Found: C, 21.22; H, 4.48; N, 8.10 and 6.1% loss on Tg analysis. FAB MS: M+H of 241.1. 300 MHz:$^1H$($D_2O$): 4.1 M(1H), 3.85 D syn/anti(3H), 3.0 M(2H) 2.9 M(2H) $^{31}P$(1H decoupled) 15+16.4 (syn/anti)

C) 4-[(Phenylmethoxy)imino]-5-phosphononorvaline 0.2 g R-4-Oxo-5-phosphononorvaline, 0.5 g O-Benzyl hydroxyamine HCl were reacted as in Example IX(A) and 4-[(phenylmethoxy)imino]-5-phosphononorvaline was obtained as a white hygroscopic powder, m.p. 153° (with decomposition), 100 mg (33%). Calcd: C 45.58; H 5.42; N, 8.86. Found: C, 40.08; H, 4.81;N, 7.67,; and 9.8% loss on Tg analysis. FAB MS: M+H 317.1. 300 MHz $^1H$ ($D_2O$) 7.45 M (5 H) 5.15 D (2H) 4.1 M (1H), 3.0 M (2H), 2.9 M (2H).

D) 4-[(2'-phenylethoxy)imino]-5-phosphononorvaline

4-[(2'-phenylethoxy)imino]-5-phosphononorvaline may be prepared using the methodology described in Example IX (A–C) but substituting R-4-oxo-5-phosphononorvaline and O-(2-phenylethyl)hydroxylamine hydrochloride as the starting materials.

EXAMPLE X

This example demonstrates the preparation of a compound of Formula Ia in which M is hydrazone.

4-(Benzylhydrazino)-5-phosphononorvaline may be prepared using the methodology of Examples IX (A–C) but substituting R-4-oxo-5-phosphononorvaline and benzylhydrazine dihydrochloride as the starting material.

EXAMPLE XI

This example demonstrates the preparation of the esters of Formula Ia.

A) R-4-Oxo-5-phosphononorvaline methyl ester

Freshly distilled acetyl chloride (25 ml) was added dropwise to dry mthanol (500 ml) at 0° C. under $N_2$ over 15 minutes. R-4-Oxo-5-phosphononorvaline (1.25 g) was added and the resulting mixture heated to the boil and refluxed for 16 hours. The resulting solution was condensed to an oil which was taken up in dry methanol (500 ml) and a slow stream of HCl passed through the solution while refluxing the solution for a further 16 hours. The resulting solution was cooled, blown to a residue with a stream of $N_2$ and then the residue eluted through a Biorad AG1X8 200–400 mesh resin (acetate form) with water. The fractions containing the desired product were freeze dried to yield 590 mg of a white solid, m.p. 88° C. (with decomposition). Anal. Calcd, C, 32.01; H, 5.37; N, 6.22. Found, C, 30/17%; H, 5.90%; N, 5.87%. TGA loss 5.7 mol %. MS(FAB) M/Z 226 (MH+). 300 MHz $^1H$ NMR ($D_2O$) 4.42 (1H, e) 3.82 (3H, S, 3.51 (2H, m) 3.14 (2H, dd). $^{31}P$ NMR ($D_2O_1$, $^1H$ decoupled) 11.4 ppm.

B) R-4-Oxo-5-phosphononorvaline ethyl ester

R-4-Oxo-5-phosphononorvaline (0.5 g) was added to anhydrous ethanol (250 ml) and the resulting mixture saturated with anhydrous HCl. The mixture was refluxed for 5 hours then cooled and evaporated to a residue. The resulting residue was taken up in water (100 ml) and then freeze dried to yield a white solid m.p. 98° C. (with decomposition). Anal Calcd C, 30.50; H, 5.49; N, 5.08. Found, C, 29.51; H, 5.69; N, 5.04. TGA loss 0.4 mol % loss. MS(FAB) M/Z 240 (MH$^+$). 300 MHz $^1$H NMR (CD$_2$O) 4.42 (1H, t) 4.29 (2H, q) 3.51 (2H, m) 3.25 (2 M, d) 1.28 (3H, t). $^{31}$P NMR (D$_2$O, $^1$H decoupled) 14.6 ppm.

What is claimed is:

1. A method for preventing or minimizing damage to nervous tissues contained within the central nervous system resulting from exposure to ischemic or hypoxic conditions selected from the group consisting of strokes, cerebrovascular accidents, carbon monoxide poisoning, cardiac arrest, drownings, suffocation and neonatal anoxic trauma comprising administering to a human patient in need thereof, a neuroprotective amount of a compound of the formula:

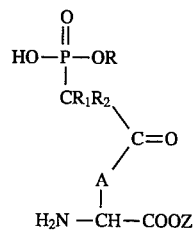

in which R is represented by $C_{1-4}$ alkyl, or —$CF_3$; $R_1$ and $R_2$ are each independently represented by hydrogen; A is represented by a methylene or a trimethylene bridging group and Z is represented by hydrogen or $C_{1-4}$ alkyl; the pharmaceutically acceptable acid addition salts thereof; the pharmaceutically acceptable basic addition salts thereof, the tautomers thereof, the optical isomers thereof, and the geometric isomers thereof.

* * * * *